(12) United States Patent
Murray

(10) Patent No.: US 12,303,179 B2
(45) Date of Patent: May 20, 2025

(54) TENSIONING INSTRUMENTS

(71) Applicant: GLOBUS MEDICAL, INC., Audubon, PA (US)

(72) Inventor: Patrick Murray, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 177 days.

(21) Appl. No.: 18/057,317

(22) Filed: Nov. 21, 2022

(65) Prior Publication Data

US 2023/0100706 A1 Mar. 30, 2023

Related U.S. Application Data

(63) Continuation of application No. 17/064,833, filed on Oct. 7, 2020, now Pat. No. 11,534,222.

(51) Int. Cl.
*A61B 17/88* (2006.01)
*A61B 17/70* (2006.01)
*A61B 17/00* (2006.01)

(52) U.S. Cl.
CPC ...... *A61B 17/8869* (2013.01); *A61B 17/7022* (2013.01); *A61B 17/7076* (2013.01); *A61B 2017/00407* (2013.01)

(58) Field of Classification Search
None
See application file for complete search history.

(56) References Cited

U.S. PATENT DOCUMENTS

| | | | | |
|---|---|---|---|---|
| 2,455,609 A | * | 12/1948 | Scheib | A61B 17/8861 606/103 |
| 4,050,464 A | * | 9/1977 | Hall | A61B 17/025 606/103 |
| 4,966,600 A | * | 10/1990 | Songer | A61B 17/8861 606/103 |
| 5,417,698 A | * | 5/1995 | Green | B25B 25/00 606/139 |
| 6,616,667 B1 | | 9/2003 | Steiger et al. | |
| 6,641,588 B2 | | 11/2003 | Citron et al. | |
| 9,113,963 B2 | | 8/2015 | Baccelli et al. | |
| 10,022,159 B2 | | 7/2018 | Simpson | |
| 10,034,692 B2 | | 7/2018 | Palmer et al. | |
| 10,188,435 B2 | | 1/2019 | Mickiewicz et al. | |
| 10,426,537 B2 | | 10/2019 | Baccelli et al. | |
| 10,568,673 B2 | | 2/2020 | Palagi et al. | |
| 10,595,904 B2 | | 3/2020 | Albert et al. | |
| 10,595,920 B2 | | 3/2020 | Simpson et al. | |
| 10,603,078 B2 | | 3/2020 | Simpson et al. | |

(Continued)

FOREIGN PATENT DOCUMENTS

| | | |
|---|---|---|
| CN | 105534581 A | 5/2016 |
| EP | 1448104 | 8/2004 |

(Continued)

*Primary Examiner* — Tessa M Matthews

(57) ABSTRACT

Tensioner instruments, systems, and methods of tensioning flexible bands in-situ. The tensioner instrument may include first and second pivoting arms with a base for pinching and pulling the flexible band to provide tension. The tensioner instrument system may include a clip inserter and a ratcheting tensioner for tensioning the band through an implant. The instruments may be configured to apply and maintain tension to the flexible band, thereby providing the desired correction to the spine.

16 Claims, 14 Drawing Sheets

(56) References Cited

U.S. PATENT DOCUMENTS

| | | | |
|---|---|---|---|
| 10,667,847 | B2 | 6/2020 | Hsu et al. |
| 2002/0169454 | A1 | 11/2002 | Citron et al. |
| 2002/0169463 | A1* | 11/2002 | Citron ................ A61B 17/8869 |
| | | | 606/148 |
| 2008/0177298 | A1 | 7/2008 | Zucherman et al. |
| 2013/0079827 | A1 | 3/2013 | Neary et al. |
| 2015/0342657 | A1 | 12/2015 | Voisard et al. |
| 2018/0289404 | A1 | 10/2018 | Shoshtaev |
| 2019/0059959 | A1 | 2/2019 | Serra et al. |
| 2020/0078055 | A1 | 3/2020 | Deneuvillers et al. |

FOREIGN PATENT DOCUMENTS

| | | | |
|---|---|---|---|
| FR | 2606312 | A | 5/1988 |
| FR | 2777449 | A | 10/1999 |
| JP | 2001187063 | A | 7/2001 |
| JP | 2004344648 | A | 12/2004 |

* cited by examiner

TENSIONING INSTRUMENTS

CROSS REFERENCE TO RELATED APPLICATION

The present application is a continuation of U.S. patent application Ser. No. 17/064,833, filed Oct. 7, 2020 (published as U.S. Pat. Pub. No. 2022-0104859), the entire disclosure of which is incorporated herein by reference in its entirety for all purposes.

FIELD OF THE INVENTION

The present application relates generally to surgical instruments, and more particularly, tensioning instruments, for example, for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. This treatment typically involves affixing screws, hooks and/or clamps to one or more vertebrae and connecting the screws, hooks and/or clamps to an elongate spinal rod that stabilizes members of the spine.

Flexible bands may be used to achieve correction and provide fixation as an alternative and/or supplement to pedicle screws during spinal deformity surgery. The bands may be wrapped around bony anatomy and then a force may be applied to secure the spine to the spinal rod. Correction of the spinal deformity may be achieved and held by application of tension to the flexible band. There exists a need for improved tensioning instruments configured to apply tension to the bands.

SUMMARY OF THE INVENTION

To meet this and other needs, instruments, systems, and methods of tensioning flexible bands in-situ are provided. After a flexible band is wrapped around bony anatomy, such as a lamina or transverse process, the instruments may be configured to apply and maintain tension to the flexible bands, thereby providing the desired correction to the spine.

According to one embodiment, a tensioner instrument for tensioning a band may include first and second pivoting arms and a base. The first and second pivoting arms may each extend from a proximal end to a distal end. The first and second pivoting arms may each include handles near the proximal ends. The base may have a generally L-shaped body coupled to the first and second pivoting arms. The base may define a slot to retain the band and/or guide the distal end of the first pivoting arm. The second pivoting arm may define an opening located beneath the slot and sized and dimensioned to receive the band. When the handles are compressed together, the band may be pinched in the slot between the distal end of the first pivoting arm and the base, and a distance between the distal ends of the arms is increased, thereby applying a tension to the band. A ratchet may be positioned between the proximal ends of the first and second pivoting arms, thereby allowing for incremental tensioning.

The tensioner instrument may include one or more of the following features. The base may include a first elongate portion and a second elongate portion angled relative to the first elongate portion at a corner. The corner of the first and second elongate portions may couple with the first pivoting arm at a first hinge. The second elongate portion of the base may terminate at a free end, which couples with the second pivoting arm at a second hinge. The first hinge may move the first pivoting arm towards the base and the second hinge may move the base away from the second pivoting arm. The first end of the ratchet may be coupled to one of the first and second pivoting arms via a pivot pin and the opposite end of the ratchet may be positionable through a slot in the other of the first and second pivoting arms. The ratchet may be a linear ratchet having a plurality of teeth along an interior of the ratchet. A pawl in the slot may be configured to engage the teeth to thereby incrementally maintain the position of the first and second pivoting arms and the amount of tension applied to the band.

According to one embodiment, a tensioner instrument may include a clip inserter and a ratcheting tensioner. The clip inserter may include a cannulated main body extending from a proximal end to a distal tip, a collar configured to translate along the main body, and a threaded shaft configured to move the collar. The ratcheting tensioner may include a fixed handle coupled to the clip inserter, a pivoting handle coupled to the fixed handle, a ratchet assembly including a pair of rotary ratchets and a spool keyed to the ratchets and positioned between the ratchets, and an actuator assembly including an actuator configured to engage the first and second rotary ratchets. When the pivoting handle is squeezed toward the fixed handle, the actuator may contact the ratchets and forces the ratchets and spool to rotate.

The tensioner instrument may include one or more of the following features. The collar may be a ring with two arms extending toward the distal tip of the main body. Each of the arms may define a notch configured to secure a spinal rod when the collar moves distally. The threaded shaft may define a hollow body such that a driver shaft is passable through the threaded shaft. The main body of the clip inserter may include a wire cut and one or more grooves on opposite sides of the wire cut configured to engage with pins on the collar. The actuator assembly may be positioned in the pivoting handle and include an actuator button for engaging and disengaging the actuator, an actuator pin for securing the actuator, and an actuator spring causing the actuator to contact the ratchets. The ratcheting tensioner may include a release assembly including a release arm pivotably coupled to the fixed handle with a pin and a release spring forcing the release arm into contact with the ratchets at rest. The release arm may include a body with a thumb press and a pair of spaced apart tongues for engaging the ratchets. The ratcheting tensioner may include a button assembly for securing the clip inserter to the ratcheting tensioner, the button assembly including a button, a button pin for securing the button, a stop pin for engaging with the body of the clip inserter, and a button spring causing the stop pin to protrude.

According to another embodiment, a system for tensioning a spinal system may include a flexible band configured to loop around a bone, a spinal rod configured for stabilizing two vertebrae, a band clamp implant having a recess for retaining the spinal rod and an opening for receiving the flexible band, and a tensioner instrument including a clip inserter and a ratcheting tensioner configured for tensioning the flexible band. The clip inserter may include a cannulated body and a collar configured to translate along the body and engage the spinal rod in a downward position. The ratcheting tensioner may include a fixed handle coupled to the clip inserter, a pivoting handle coupled to the fixed handle, a ratchet assembly including a ratchet and a spool keyed to the ratchet, and an actuator configured to engage the ratchet. When the pivoting and fixed handles are squeezed together, the actuator may force the ratchet and spool to rotate, thereby applying tension to the flexible band.

According to yet another embodiment, a method for tensioning a spinal system, in situ, may include one or more of the following steps in any suitable order: (1) looping a flexible band around a portion of bone, such as a lamina or transverse process; (2) threading the band through an implant; (3) affixing the implant to the clip inserter; (4) positioning the implant against a spinal rod and securing the clip inserter to the spinal rod; (5) threading the band through the spool; (6) positioning the tensioner against the implant; (7) squeezing the handles of the tensioner together causing the spool to rotate and wrapping the band around the spool, thereby applying controlled, incremental tension to the band; (8) once the desired tension has been reached, securing the band in the implant (e.g., with a set screw); and (9) removing the instrument from the patient.

Also provided are kits including implants of varying types and sizes, rods, tensioner instruments of varying types and configurations, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to instrument, systems, and methods for tensioning flexible bands in-situ. Specifically, embodiments are directed to instruments and systems configured to tension a flexible band in order to provide fixation to the spine.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

Referring now to FIGS. 1-7, a handled tensioner instrument 10 is shown according to one embodiment. The tensioner 10 is configured to apply tension to an elongate member, cable, tether, cord, or band 12. The band 12 may be a flexible member configured to be wrapped around bony anatomy or a portion of the spine, such as the lamina or transverse process, for example. Although described with reference to the spine, it will be appreciated that the instruments and systems described herein may be applied to other orthopedic locations and applications, such as trauma.

The flexible band 12 may be able to adapt to complex anatomies, such as severe spinal deformities. The band 12 may be used alone or in conjunction with an implant 14, such as a screw (e.g., a pedicle screw), a clamp, a hook, or other suitable implant. The implant 14 may engage with an elongate member, such as a spinal rod, to provide fixation between vertebrae. In this embodiment, the implant 14 is shown as a pedicle screw with a tulip for receiving a spinal rod and a clamp for retaining the band 12. Examples of other implants and rod constructs are described in more detail, for example, in U.S. Pat. Nos. 9,433,441; 10,034,692; 10,548,644; and 10,575,879, which are incorporated by reference herein in their entireties for all purposes. After the implant 14 is affixed to bone and/or secured to bone by looping the band 12 around the bony anatomy, correction of the spinal deformity may be achieved and held by the application of tension to the flexible band 12.

The band 12 may be comprised of polyethylene terephthalates (PET), polyethylenes (e.g., ultrahigh molecular weight polyethylene or UHMWPE), polypropylenes, silk, polyamides, polyesters, polyacrylonitriles, silk cottons, combinations thereof, or other suitable biocompatible materials. The band 12 may be generally round, oval, or flat/tape geometry. The band 12 may transition from one geometry to another (e.g., a round to flat geometry or vice versa). If desired, the band 12 may be fully radiolucent or may have one or more marker strands that are designed to show up on fluoroscopy.

Figure 1:
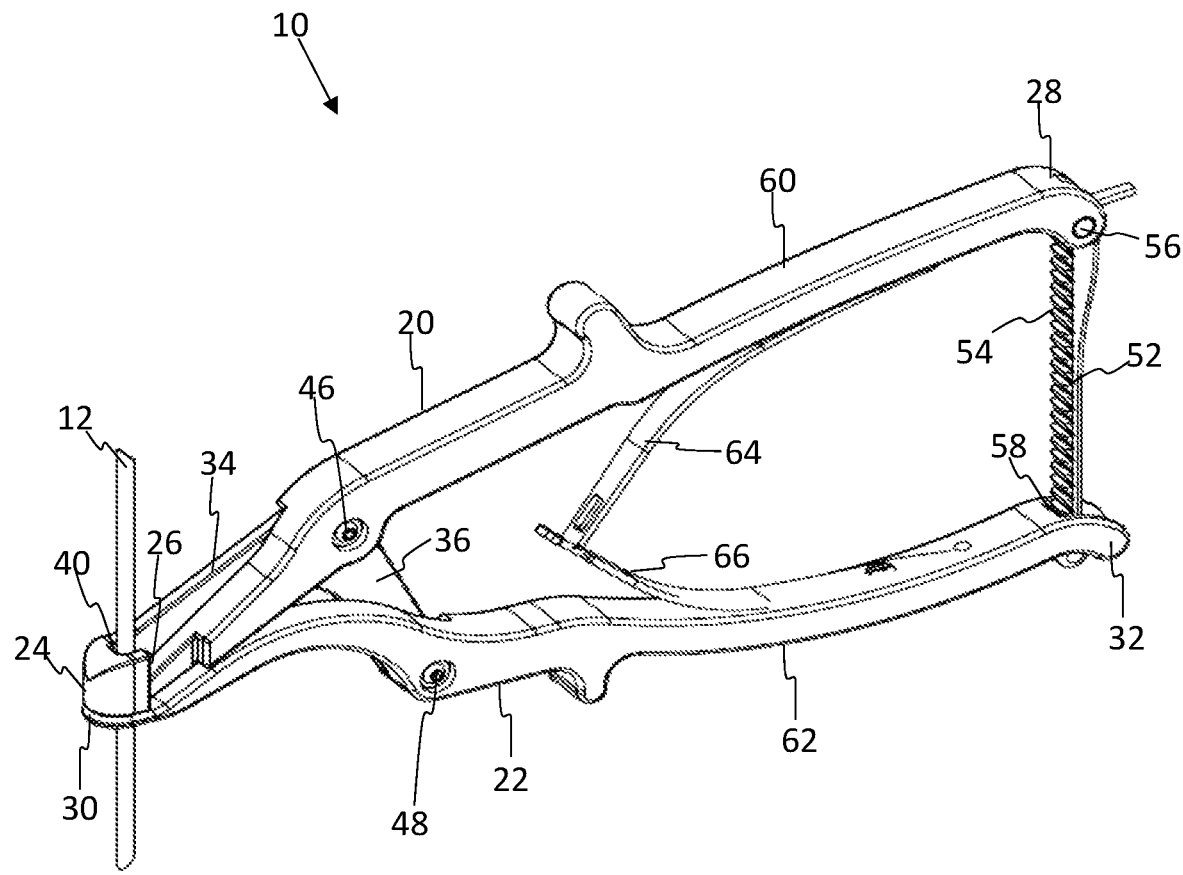
FIG. 1 shows a perspective view of a handled tensioner instrument able to pinch and pull the flexible band to provide tension according to one embodiment.

With emphasis on FIG. 1, the tensioner 10 pinches and pulls the flexible band 12 in order to provide tension. The tensioner 10 includes an upper handle arm or first pivoting arm 20, a lower handle arm or second pivoting arm 22, and a base 24. The first pivoting arm 20 extends from a first end or distal end 26 to a second end or proximal end 28. Similarly, the second pivoting arm 22 extends from a distal end 30 to a proximal end 32. The base 24 and distal ends 26, 30 form the tip of the instrument 10, which is configured to access the patient in-situ. The proximal ends 28, 32 are manipulable by a user, such as a surgeon. The first and second pivoting arms 20, 22 may each define a handle 60, 62, for example, near the proximal ends 28, 32, which are configured to be gripped and squeezed by the user. The inner facing portions of the handles 60, 62 may include curved leaf springs 64, 66 configured to apply an opposing force to the handles 60, 62 when squeezed.

Figure 6:
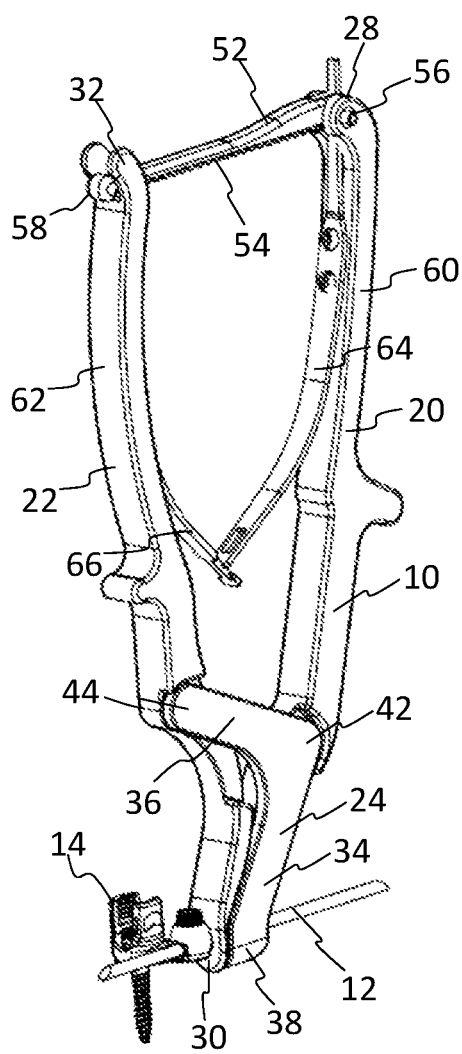
FIG. 6 shows a perspective view of an implant with the tensioner instrument in the relaxed position retaining the band.
Figure 7:
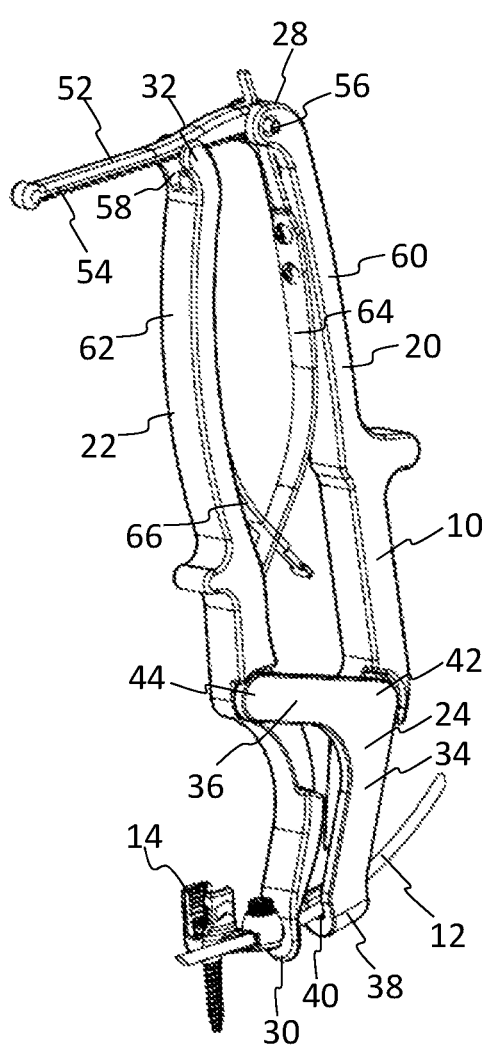
FIG. 7 shows a perspective view of the implant with the tensioner instrument in the tensioned position, thereby applying a force to the band.
Figure 8:
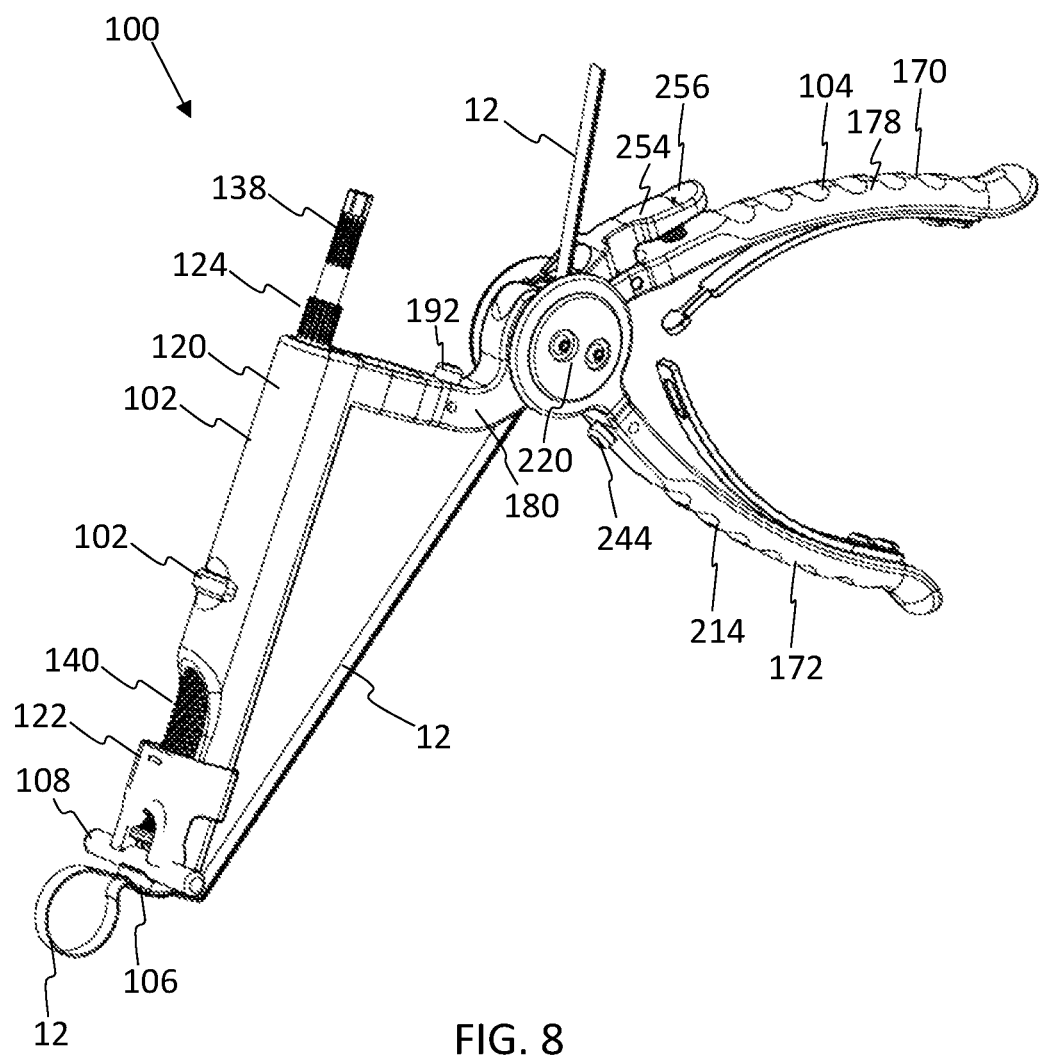
FIG. 8 shows a perspective view of a tensioner instrument system including a clip inserter and a ratcheting tensioner with a band extending therethrough according to one embodiment.
Figure 9:
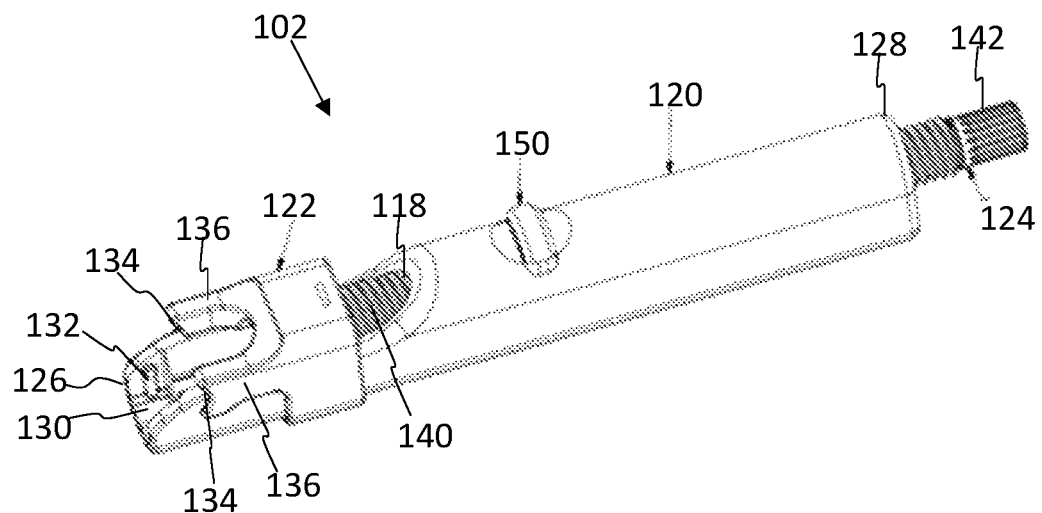
FIG. 9 shows a perspective view of the clip inserter of FIG. 8.

As best seen in FIGS. 6 and 7, the base 24 may have a generally L-shaped body. For example, the base 24 may have a first elongate portion 34 and a second elongate portion 36 angled relative to the first elongate portion 34. A distal portion or first end 38 of the first elongate portion 34 of the base 24 may define a channel or slot 40 configured to retain the band 12 and/or guide the distal end 26 of the first arm 20. The second end 42 of the first elongate portion 34 of the base 24 integrally connects to the second elongate portion 36. The corner or second end 42 of the first elongate portion 34 of the base 24 may mate with the first arm 20. The second elongate portion 36 of the base 24 terminates at a proximal end or free end 44, which may be configured to mate with the second arm 22.

Figure 2:
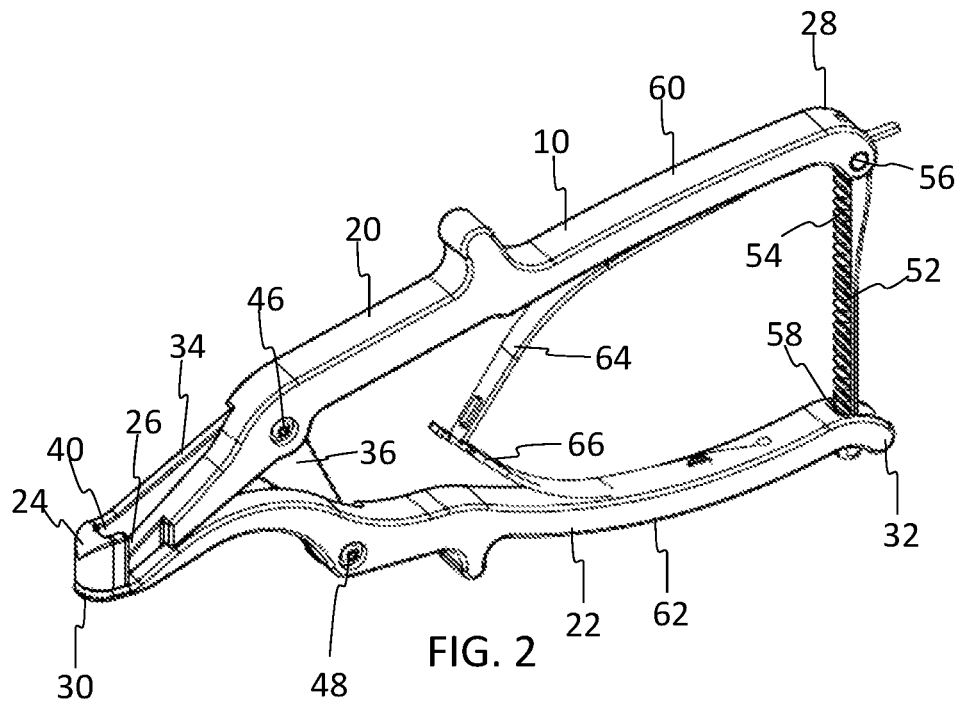
FIG. 2 shows a perspective view of the tensioner instrument of FIG. 1 in a closed or relaxed position.
Figure 3:
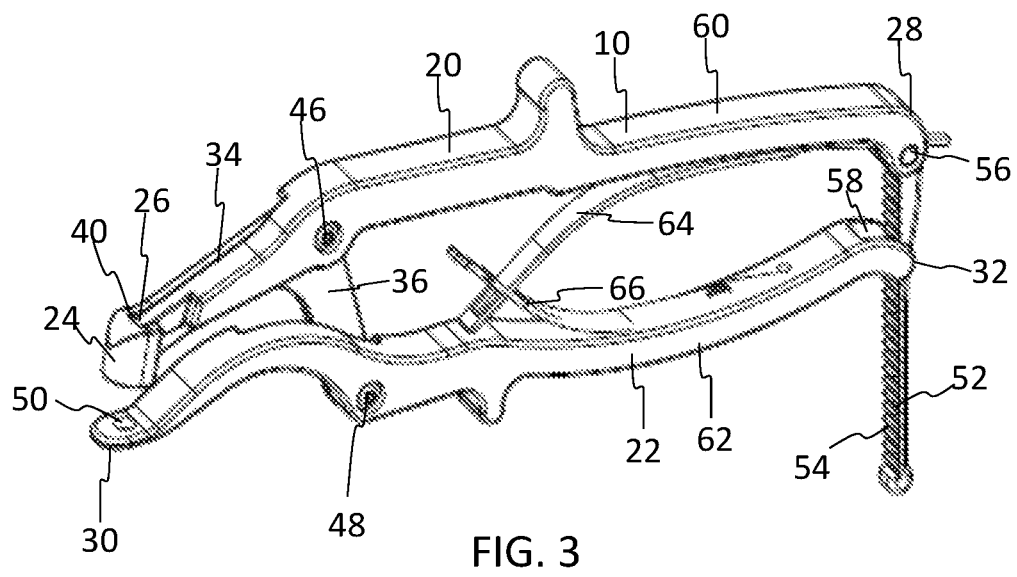
FIG. 3 shows a perspective view of the tensioner instrument of FIG. 1 in an open or tensioned position.

As shown in FIGS. 2 and 3, the instrument 10 may include a ratchet 52 positionable between the proximal ends 28, 32 of the upper and lower pivoting arms 20, 22 to hold tension applied to the flexible band 12. The ratchet 52 may include a linear body or rail with a plurality teeth 54 defined along the interior of the ratchet 52. A first end of the ratchet 52 may be coupled to one of the pivot arms 20, 22 via a pivot pin 56 and the opposite end of the ratchet 52 may be positionable through a slot or opening 58 in the body of the other pivot arm 20, 22. In FIG. 2, the tensioner 10 is shown in a first relaxed position where tension would not be applied to the band 12. In FIG. 3, the tensioner 10 is shown in a second tensioned position where tension would be applied to the band 12. As the ratchet 52 moves through the opening 58, a pawl in the opening 58 engages the teeth 54 to thereby incrementally maintain the position of the arms 20, 22 and the amount of tension applied to the band 12.

Figure 4:
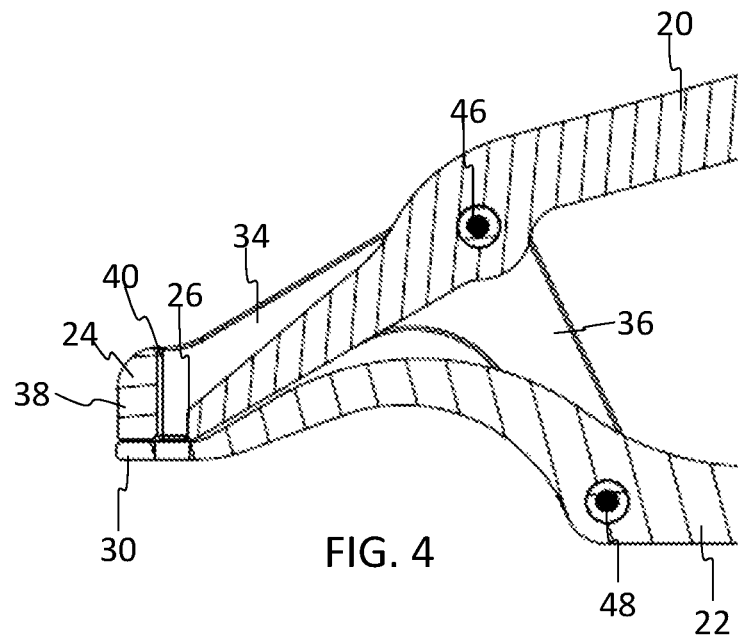
FIG. 4 is a close-up cross-sectional view of the distal tip of the tensioner instrument in the relaxed position.
Figure 5:
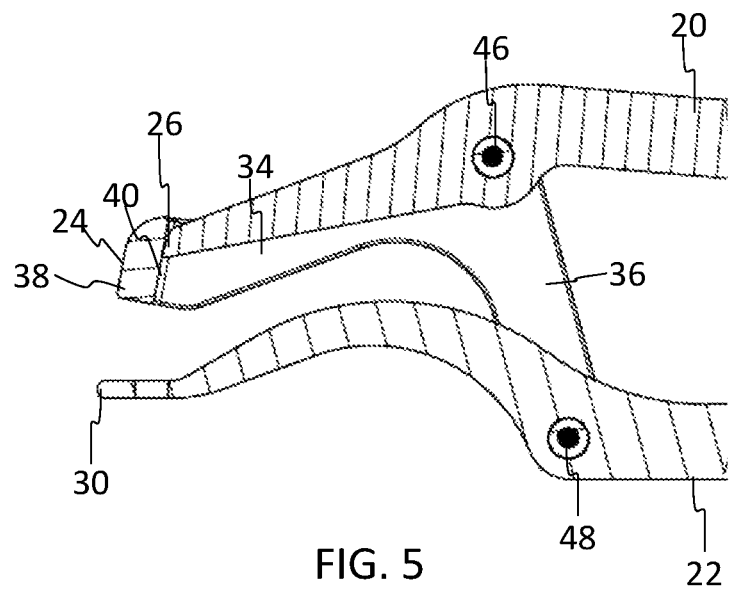
FIG. 5 is a close-up cross-sectional view of the distal tip of the tensioner instrument in the tensioned position.

With emphasis on FIGS. 4 and 5, the base 24 may be fixed to each pivoting arm 20, 22 to create two hinges 46, 48. The first hinge 46 connects the base 24 to the first arm 20, for example, at the corner 42 connecting the first and second elongate portions 34, 36 of the base 24. The second hinge 48 connects the base 24 to the second arm 22, for example, at the free end 44 of the second elongate portion 36 of the base 24. The hinges 46, 48 may each include a pivot pin. Although pivot pins are exemplified in this embodiment, it will be appreciated that other suitable joints could be selected.

The first hinge 46 moves the upper pivoting arm 20 toward the base 24, while the second hinge 48 moves the base 24 away from the lower pivoting arm 22. The distal end 26 of the upper pivoting arm 20 may include geometry configured to move within the slot 40 in the base 26. In the rest/relaxed position shown in FIG. 4, there is clearance between the distal end 26 of the upper pivoting arm 20 and the base 26 (slot 40). When the handles 60, 62 are squeezed into the tensioned position as shown in FIG. 5, the upper pivoting arm 20 moves toward the base 24, decreasing the clearance between the upper pivoting arm 20 and the base 26 until the upper pivoting arm 20 contacts the base 24 and travels along slot 40. In this manner, the band 12 residing in slot 40 is pinched between the distal end 26 of the arm 20 and the base 24.

As best seen in FIG. 3, the lower pivoting arm 22 has a thru hole 50 configured to accept the flexible band 12. The thru hole 50 is located directly beneath the slot 40 in the base 26, thus allowing the flexible band 12 to be passed through the hole 50 in the lower pivoting arm 22 and into the slot 40 in the base 26. When the handles 60, 62 are squeezed, the upper pivoting arm 20 pinches the flexible band 12 against the base 26 and the lower pivoting arm 22 pushes the contacting surface away from the base 26, thus providing tension to the flexible band 12.

As seen in FIGS. 6 and 7, the lower pivoting arm 22 may be placed against the implant 14 in order to tension the flexible band 12 through the implant 14. As the handles 60, 62 are compressed, the distance between the distal ends 26, 30 of the arms 20, 22 is increased, and a tension is applied to the band 12. The ratchet 52 between the upper and lower pivoting arms 20, 22 holds and maintains the tension applied to the band 12.

During the procedure, the implant 14 may be secured to bone. In this embodiment, the implant 14 includes a pedicle screw with a tulip for receiving a spinal rod and an attached clamp for receiving the band 12. It will be appreciated that other suitable implants may be selected. The band 12 may be threaded through the tensioner 12 and the implant 14. The band 12 may be looped around a portion of bone, such as the lamina. A tension may be applied to the band 12 by squeezing the handles 60, 62 of the tensioner 12 toward one another. The ratchet 52 allows for controlled, incremental tensioning of the band 12. Once the desired tension has been reached, the band 14 may be secured by the implant 12 (e.g., with a set screw in the clamp), and the instrument 10 may be removed from the patient.

Turning now to FIGS. 8-23, an embodiment of a tensioner instrument system 100 is shown. The tensioner system 100 includes a clip inserter 102 and a ratcheting tensioner 104, which are configured to mate together and apply tension to the band 12. Although the tensioner system 100 is described with respect to two separate components, it will be appreciated that the instrument 100 may comprise a single integral body. The tensioner system 100 is configured to insert an implant 106 onto a spinal rod 108 and tension the flexible band 12 through the implant 106.

Figure 10:
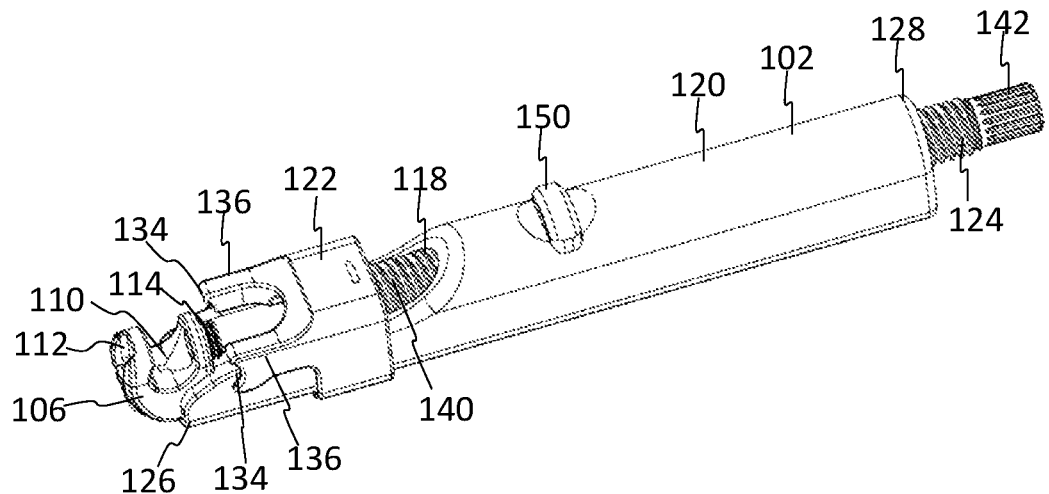
FIG. 10 shows a perspective view of the clip inserter engaging a band clamp implant.
Figure 11:
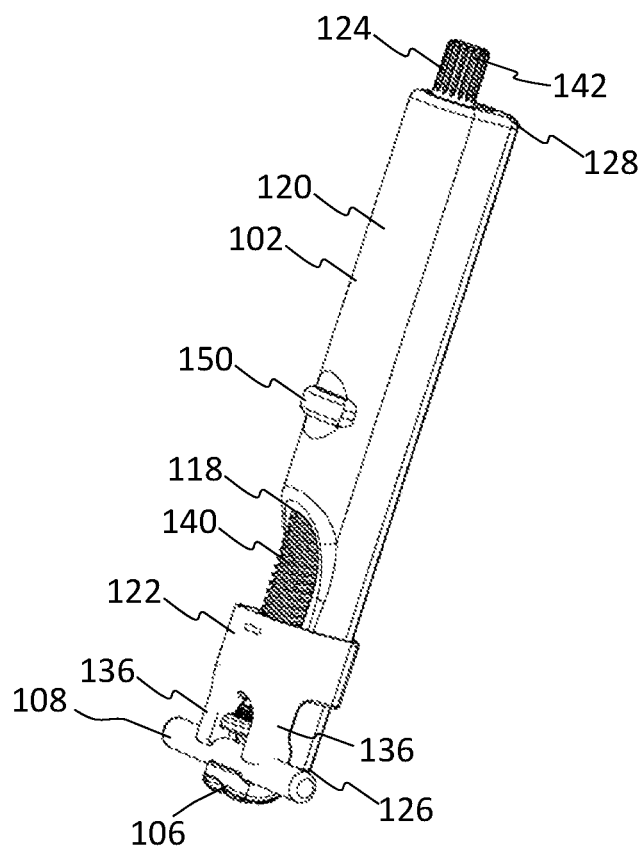
FIG. 11 shows a perspective view of the clip inserter and band clamp engaged with the spinal rod.

As best seen in FIG. 10, the implant 106 may be a band clamp implant having a generally c-shaped body with a recess 110 for retaining the rod 108, one or more openings 112 for receiving the band 12, and a locking member or set screw 114 for retaining the band 12 in the implant 106 and maintaining tension applied to the band 12. Although the band clamp implant 106 is exemplified in this embodiment, it will be appreciated that the tensioner system 100 is configured to interface with other implants and apply tension to the band 12. Examples of additional implants and rod constructs are described in more detail, for example, in U.S. Pat. Nos. 9,433,441; 10,034,692; 10,548,644; and 10,575,879, which are incorporated by reference herein in their entireties for all purposes.

Turning now to FIGS. 9-15, the clip inserter 102 includes a main body 120, a collar 122, and a threaded shaft 124 extending through the main body 120. With emphasis on FIG. 9, the clip inserter 102 has a main body 120 extending from a tip or distal end 126 to a proximal end 128. The main body 120 may be in the form of a hollow outer tube or cannula defining a central channel 118 between its distal and proximal ends 126, 128. The body 120 defines a recess 130 at the distal tip 126 which is configured to accept the band clamp implant 106. The recess 130 may define one or more protrusions 132 configured to engage with a corresponding mating groove on the band clamp implant 106.

Figure 13:
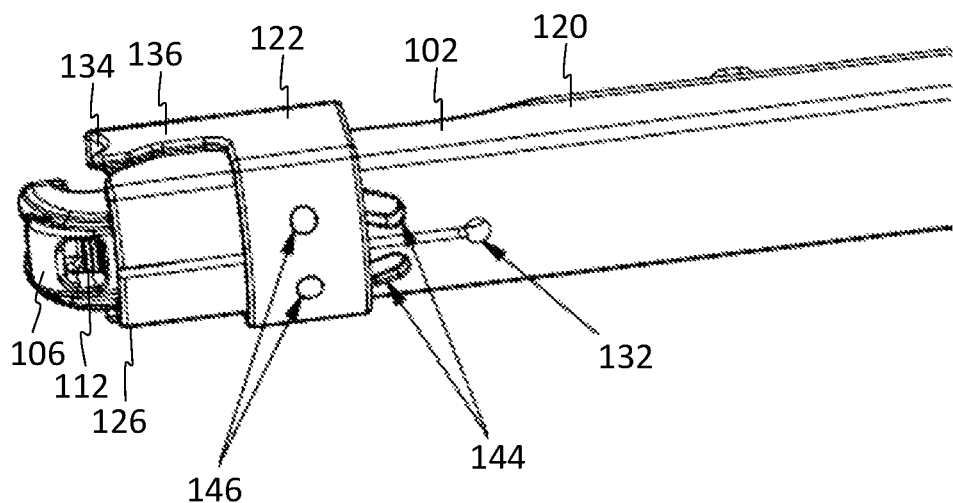
FIG. 13 is a partial bottom view of the clip inserter showing a wire cut and collar pins in release grooves the body of the clip inserter.

As shown in FIG. 10, the implant 106 is receivable in the recess 130 and mates with the protrusions 132 such that the implant 106 is retained at the distal end 126 of the main body 120 of the clip inserter 102. It will be appreciated that the implant 106 may be coupled to the tip 126 of the clip inserter 102 in any suitable manner. As shown in FIG. 13, a bottom surface of the main body 120 toward its distal end 126 may include a wire cut 132. The wire cut 132 may extend along a longitudinal axis of the body 120 from the distal end 126 inward a distance past the collar 122 of the clip inserter 102. The wire cut 132 allows the clip inserter 102 to splay open to accept and release the implant 106.

Figure 12:
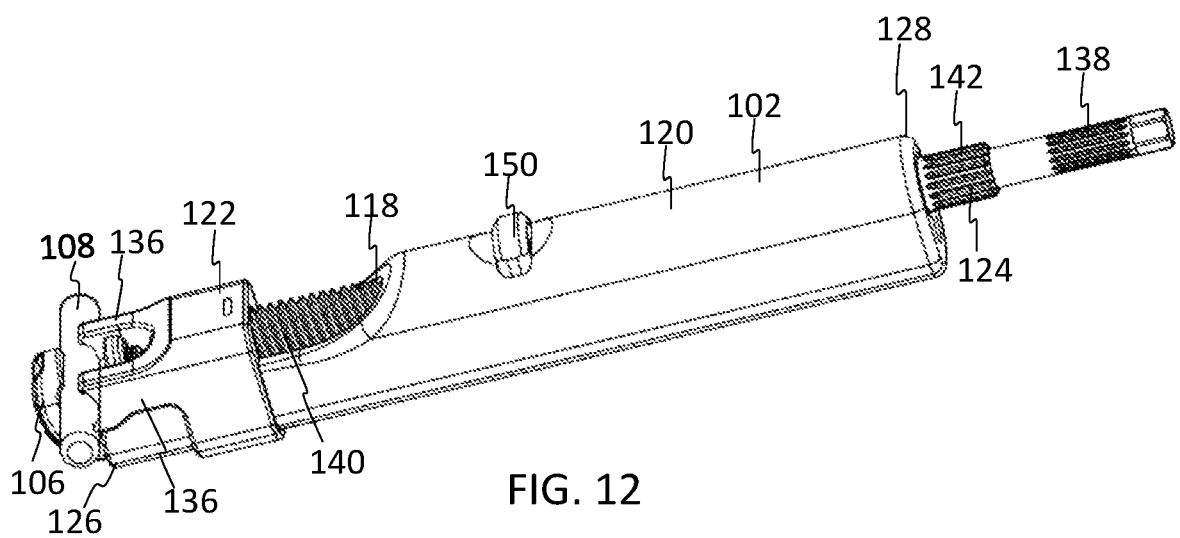
FIG. 12 shows a side perspective view of the clip inserter, band clamp implant, and spinal rod with a driver shaft configured to engage with a set screw on the top of the band clamp.

The clip inserter instrument 102 has a collar 122 that is able to translate up and down the instrument 102 to engage and disengage with the spinal rod 108. In the upward position, the collar 122 is disengaged from the rod 108. In the downward position, the collar 122 is engaged with the rod 108. The collar 122 may be a ring with a hollow center such that the main body 120 is received through the collar 122. Toward the distal end 126 of the body 120, the collar 122 may include one or more notches 134 configured to engage the spinal rod 108 when the collar 122 is in the downward position (as shown in FIG. 12). The collar 122 may include a pair of spaced apart arms 136 which define the notches 134 at the free ends of the arms 136. When the collar 122 moves distally, the notches 134 engage with the outer surface of the rod 108, thereby securing the rod 108 to the clip inserter 102.

The collar 122 is able to translate up and down the instrument 102 via engagement with the threaded shaft 124. The threaded shaft 124 is receivable through the channel 118 in the main body 120. The threaded shaft 124 may define a hollow body such that a driver shaft 138 is passable through the center of the threaded shaft 124. The threaded shaft 124 includes a threaded portion 140 along the length of the shaft 124. The threaded portion 140 may have one or more threads of suitable diameter, handedness, thread form, thread angle, lead, pitch, etc. The threaded shaft 124 and collar 122 may cooperate as a ball screw, leadscrew, or other suitable translation mechanism. The proximal end of the shaft 124 may include a handle interface 142 (e.g., a ribbed portion) configured to mate with a handle (not shown). When the threaded shaft 124 is rotated, the collar 122 is translated upward to the disengaged position or downward to the engagement position with the rod 108.

The threaded shaft 124 may be rotated in a first direction to translate the collar 122 downward. Actuation of the threaded shaft 124 pushes the collar 122 into contact with the spinal rod 108, which is contacted on the underside by the band clamp implant 106. These contact forces allow the band clamp implant 106 to be rigidly held in place on the spinal rod 108. The threaded shaft 124 is cannulated to accept the driver shaft 138, which is configured for tightening the set screw 114 on the band clamp 106. The driver shaft 138 may also include a handle interface configured to mate with a handle (not shown).

As visible in FIG. 13, the main body 120 of the clip inserter 102 may include one or more grooves 144 configured to engage with pins 146 on the collar 122. In particular, a pair of angled grooves 144 may be positioned on either side of the central wire cut 132. The grooves 144 in the main body 120 may be angled inward toward the proximal end 128 and outward toward the distal end 126. The angled grooves 144 allow the pins 146 in the collar 122 to force the distal end 126 of the body 120 to splay open when the collar 122 is pulled into the upward position, thereby releasing the implant 106 from the clip inserter 102.

Figure 14:
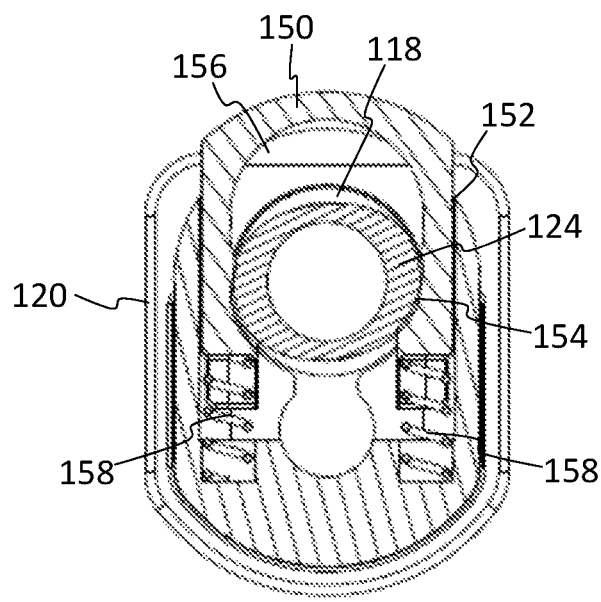
FIG. 14 is a close-up cross-sectional view of the button in the clip inserter, at rest, with the threaded shaft engaged with the button.
Figure 15:
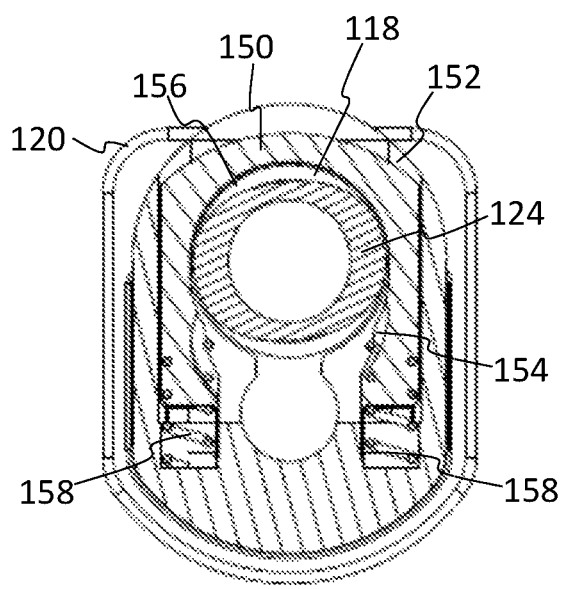
FIG. 15 is a close-up cross-sectional view of the button depressed in the clip inserter and the threaded shaft disengaged.

With emphasis on FIGS. 14 and 15, the clip inserter 102 may include a button 150 which is positioned within a slot 152 within the main body 120. An inner portion of the button 150 may define a clearance hole 156 and threads 154 configured to engage the threaded shaft 124. The button 150 may be held in place by a pin and contacts one or more springs 158. In the rest position shown in FIG. 14, the threads 154 inside the button 150 engage the threaded portion 140 of the threaded shaft 124. When the button 150 is depressed as shown in FIG. 15, the clearance hole 156 allows the threaded shaft 124 to translate freely through the button 150.

Figure 16:
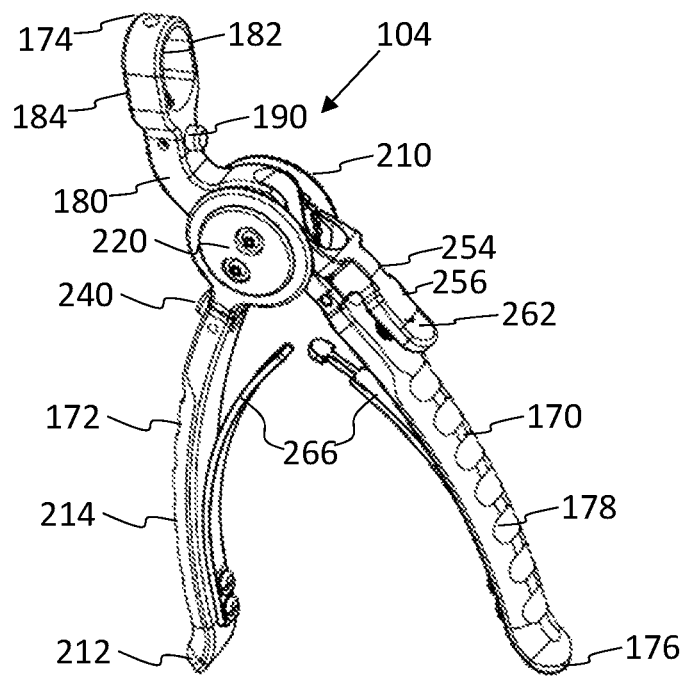
FIG. 16 shows a perspective view of the ratcheting tensioner of FIG. 8.
Figure 17:
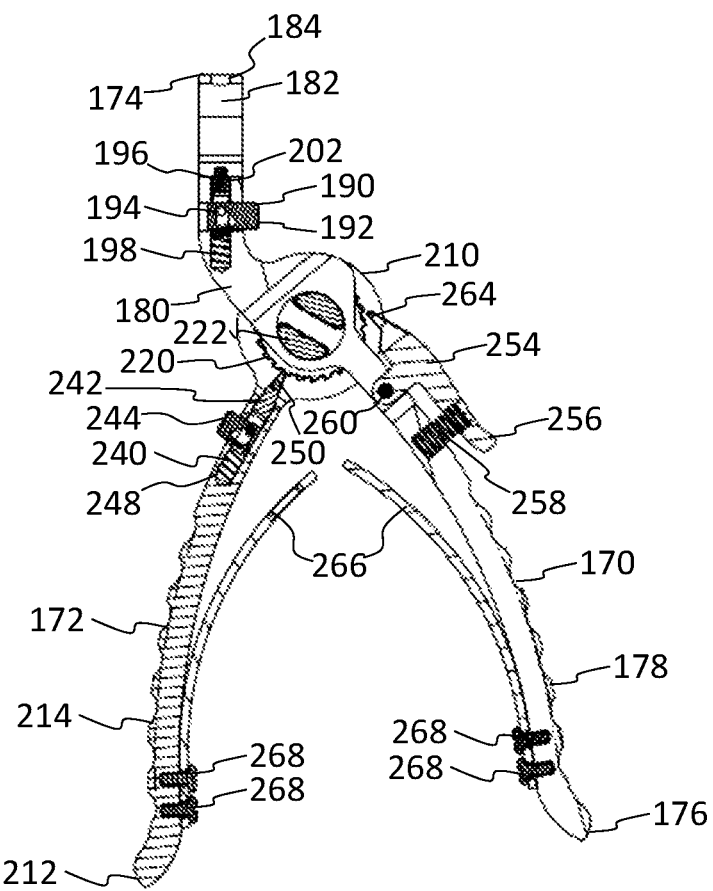
FIG. 17 is cross-sectional view of the ratcheting tensioner.
Figure 18:
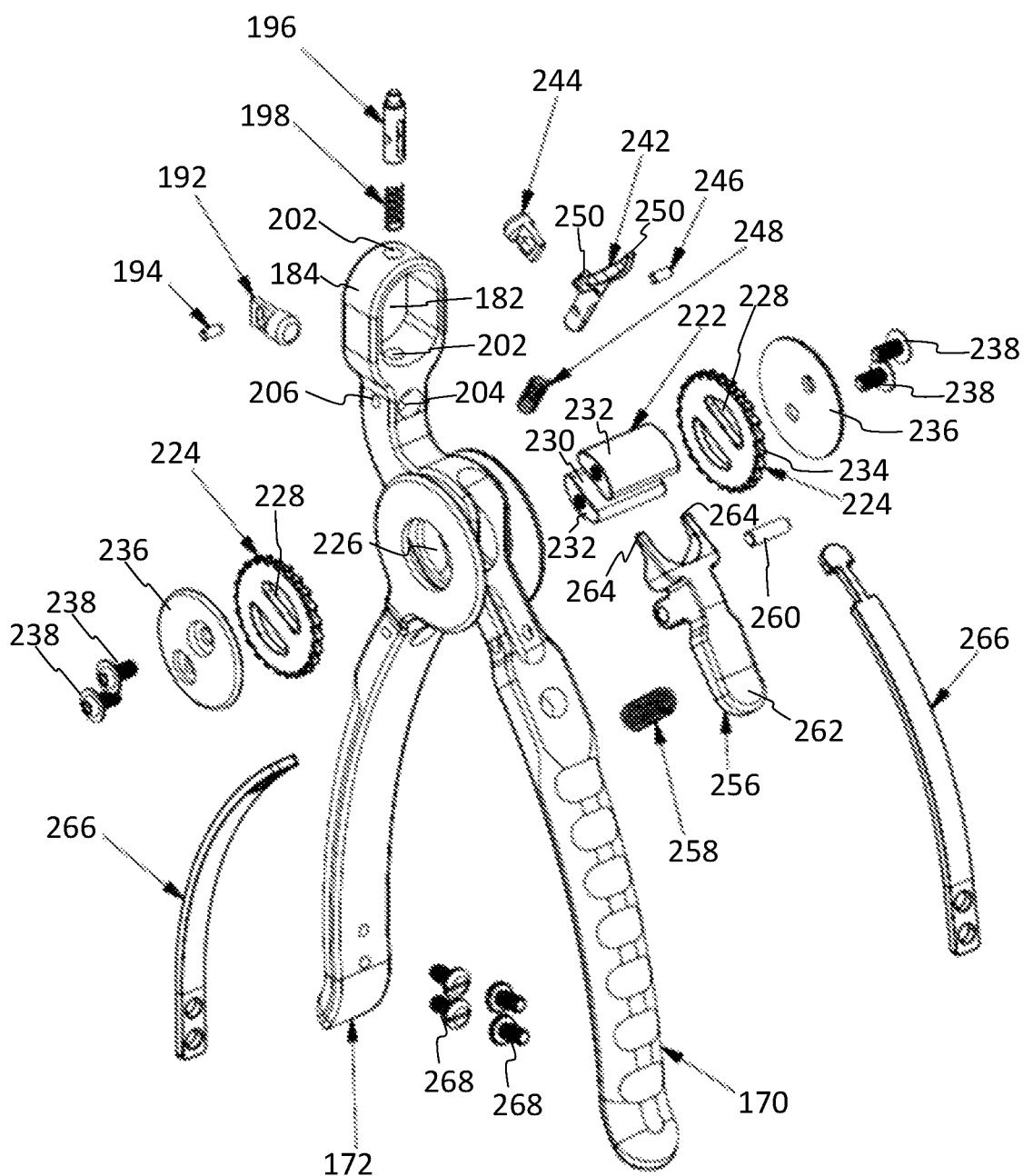
FIG. 18 is an exploded view of the ratcheting tensioner.
Figure 19:
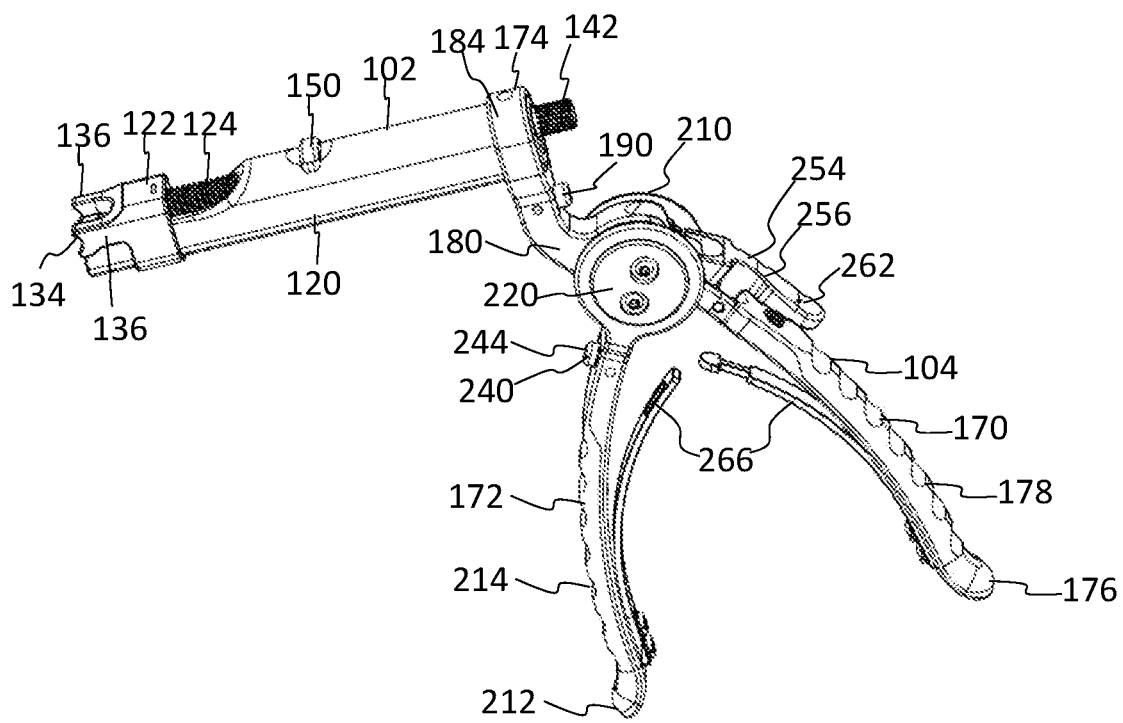
FIG. 19 shows a perspective view of the ratcheting tensioner mated with the clip inserter.

Turning now to FIGS. 16-23, the tensioner system 100 includes a ratcheting tensioner 104. The ratcheting tensioner 104 is a handled instrument which uses a ratchet assembly 220 to rotate a spool 222 in order to wind up the band 12, thereby providing tension to the band 12. An exploded view of the ratcheting tensioner 104 is shown in FIG. 18. The ratcheting tensioner 104 may include a fixed handle 170, a pivoting handle 172, and a ratchet assembly 220 with an actuator assembly 240 and a release assembly 254.

With emphasis on FIG. 16, the ratcheting tensioner 104 has a fixed handle 170 and a pivoting handle 172. The fixed handle 170 extends from a distal end 174, which is configured to couple to the clip inserter 102, to a proximal end 176. The proximal end 176 includes a handle portion 178 configured to be manipulated by the user. A neck 180 connects the distal portion 174 to the handle portion 178. The neck 180 may be bent or angled upwards to provide a pistol grip orientation for the ratcheting tensioner 104 when assembled to the clip inserter 102 and used to tension the band 12. For example, the neck 180 may be curved back toward the fixed handle 170. The distal portion 174 of the fixed handle 170 may define an opening or through slot 182 configured to receive the main body 120 of the clip inserter 102. The distal portion 174 may include a ring or loop 184 defining the slot 182 for retaining the clip inserter 102. For example, the body 120 of the clip inserter 102 may be inserted through the slot 182 in the fixed handle 170 near the proximal end 128 of the clip inserter 102.

Figure 20:
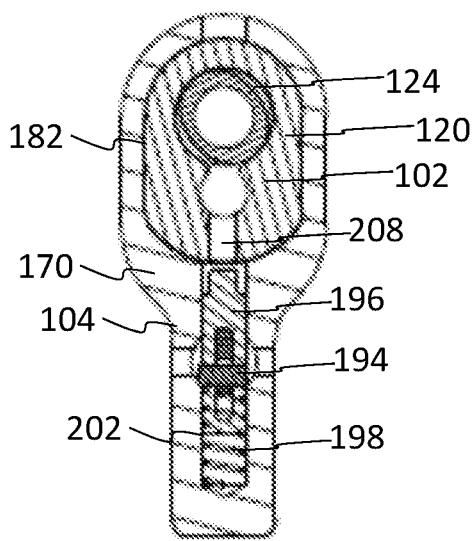
FIG. 20 is a cross-sectional view of the ratcheting tensioner and clip inserter showing the button depressed and the stop pin disengaged from the clip inserter.
Figure 21:
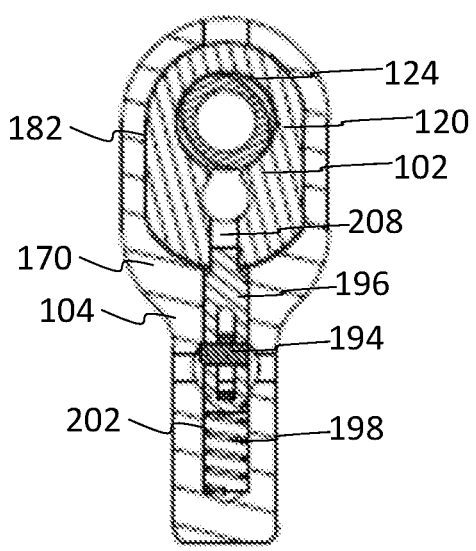
FIG. 21 is a cross-sectional view of the ratcheting tensioner and clip inserter showing the button at rest and the stop pin engaged with the clip inserter.

As shown in FIGS. 17 and 18, the ratcheting tensioner 104 may be coupled to the clip inserter 102 with a button assembly 190. The button assembly 190 may include a button 192, a button pin 194 for securing the button 192, a stop pin 196 for engaging with the body 120 of the clip inserter 102, and a button spring 198 causing the stop pin 196 to protrude into the slot 182. Intersecting the slot 182 is a bore 202 sized and dimensioned to accept the button spring 198 and the stop pin 196. At rest, the button spring 198 causes the stop pin 196 to protrude into the slot 182 which accepts the clip inserter 102. The fixed handle 170 has a first through hole 204 sized and dimensioned to accept the button 192 and a second transverse through hole 206 configured to accept the button pin 194. The button 192 is coupled to the stop pin 196 with the button pin 194 such that the stop pin 196 translates back into the fixed handle 170 when the button 192 is depressed. When the button 192 is depressed as shown in FIG. 20, the stop pin 196 retracts and the fixed handle 170 may be engaged onto the clip inserter 102. When the button 192 is released as shown in FIG. 21, the stop pin 196 translates and extends outwardly into a mating hole 208 on the clip inserter 102 to securely couple the ratcheting tensioner 104 to the clip inserter 102.

The pivotable handle 172 extends from a distal end 210, which couples to the fixed handle 170, to a proximal end 212. The proximal end 212 includes a handle portion 214 configured to be manipulated by the user. The distal end 210 is pivotably coupled to the fixed handle 170 with a ratchet assembly 220. The pivotable handle 172 and fixed handle 170 are sized and dimensioned to retain the ratchet assembly 220.

The ratchet assembly 220 includes a spool 222 and at least one rotary ratchet 224. For example, the assembly 220 may include first and second rotary ratchets 224 positionable on opposite sides of the spool 222. The spool 222 includes two half rounds or halves 232 with a space or gap 230 separating the two halves 232. The outer surfaces of the halves 232 may be curved or rounded. Each rotary ratchet 224 may include a round gear having a plurality of teeth 234 around the perimeter of the ratchet 224. The teeth 234 may be uniformly distributed around the body of the ratchet 224. The actuator 242 is configured to engage the teeth 234 as the ratchets 224 rotate. The teeth 234 may be sloped or angled to allow the actuator 242 to slide up and over the teeth 234 and into the depression between teeth 234 when the ratchets 224 rotate in a first direction. When the ratchets 224 try to move in an opposite direction, the actuator 242 catches against the first tooth 234, thereby locking the actuator 242 against the tooth 234 and preventing any further motion in that direction. The ratchet assembly 220 is secured to the handles 170, 172 with first and second cap plates 236 positioned on the outer sides of the ratchets 224. A plurality of fasteners 238, such as set screws, may be used to secure the cap plates 236 and the entire assembly.

Each handle 170, 172 has a thru hole 226 sized and dimensioned to accept the spool 222. The two ratchets 224 sit between the pivoting handle 172 and the fixed handle 170 on either side of the fixed handle 170. Each ratchet 224 defines two cutouts 228 configured to accept the two halves of the spool 222. The spool 222 is able to rotate independently of the handles 170, 172, but the spool 222 is keyed to the ratchet 224 such that the spool 222 rotates when the ratchet 224 rotates. The space or gap 230 between the two halves of the spool 222 is large enough to accept the flexible band 12.

The actuator assembly 240 includes an actuator 242 for engaging with the ratchets 224, an actuator button 244 for engaging and disengaging the actuator 242, an actuator pin 246 for securing the actuator 242, and an actuator spring 248 causing the actuator 242 to contact the ratchets 224. The actuator 242 includes a body with two spaced apart pawls 250. Each pawl 250 is configured to engage with teeth 234 on the respective ratchets 224. The pivoting handle 172 has a bore to accept the actuator 242 and actuator spring 248. The actuator spring 248 forces the actuator 242 to contact the ratchets 224 in the resting position. The pivoting handle 172 has two transverse thru holes to accept the actuator button 244 and the actuator button pin 246. The actuator button 244 is coupled to the actuator 242 with the actuator pin 246 such that when the button 244 is depressed, the actuator 242 translates away from the ratchets 224, thereby disengaging the actuator 242 from the ratchets 224.

The release assembly 254 includes a release arm 256, a release spring 258, and a release pin 260 for pivotably securing the release arm 256. The release arm 256 include a body with a thumb press 262 and a pair of spaced apart tongues 264 for engaging the ratchets 224. The release arm 256 is pivotably coupled to the fixed handle 170. The release arm 256 is positioned within a slot and is secured by pivot pin 260. The release arm 256 defines a counter bore to accept the release spring 258. The release spring 258 forces the tongues 264 of the release arm 256 into contact with the ratchets 224 at rest. The tongues 264 of the release arm 256 may be disengaged from the ratchets 224 by depressing the release arm 256, thereby compressing the release spring 258 and pivoting the tongues 264 out of contact with the ratchets 224.

The ratcheting tensioner 104 may include a pair of leaf springs 266 coupled to the handles 170, 172 with one or more fasteners 268, such as a plurality of set screws. The curved leaf springs 266 cause the handles 170, 172 to remain open at rest. When the handles 170, 172 are squeezed together, the actuator 242 on the pivoting handle 172 contacts the ratchets 224 and forces the ratchets 224 and spool 222 to rotate. While the ratchet 224 is rotating, the release arm 256 on the fixed handle 170 is lifted into consecutive ratchet positions. When the handles 170, 172 are released, the leaf springs 266 cause the handles 170, 172 to open and the actuator 242 on the pivoting handle 172 lifts back into consecutive ratchet positions. The spool 222 is held in the new orientation and does not rotate back with the opening pivoting handle 172 because the release arm 256 on the fixed handle 170 is engaged with the ratchet 224. This process is repeated causing the spool 222 to rotate within the ratcheting tensioner 104, thereby applying tension to the band 12.

Figure 22:
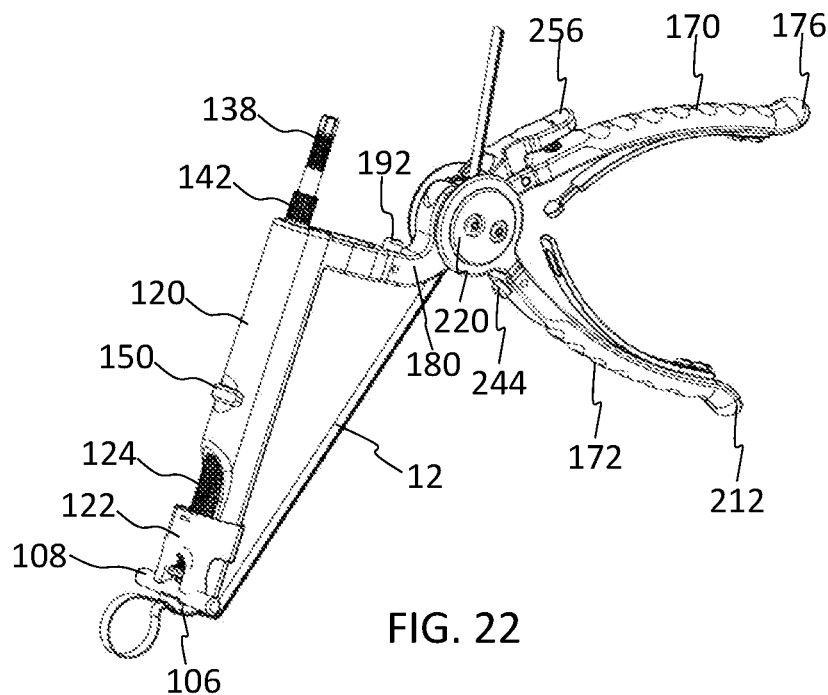
FIG. 22 shows a flexible band fed through the band clamp implant attached to the clip inserter and fed through the spool of the ratcheting tensioner.
Figure 23:
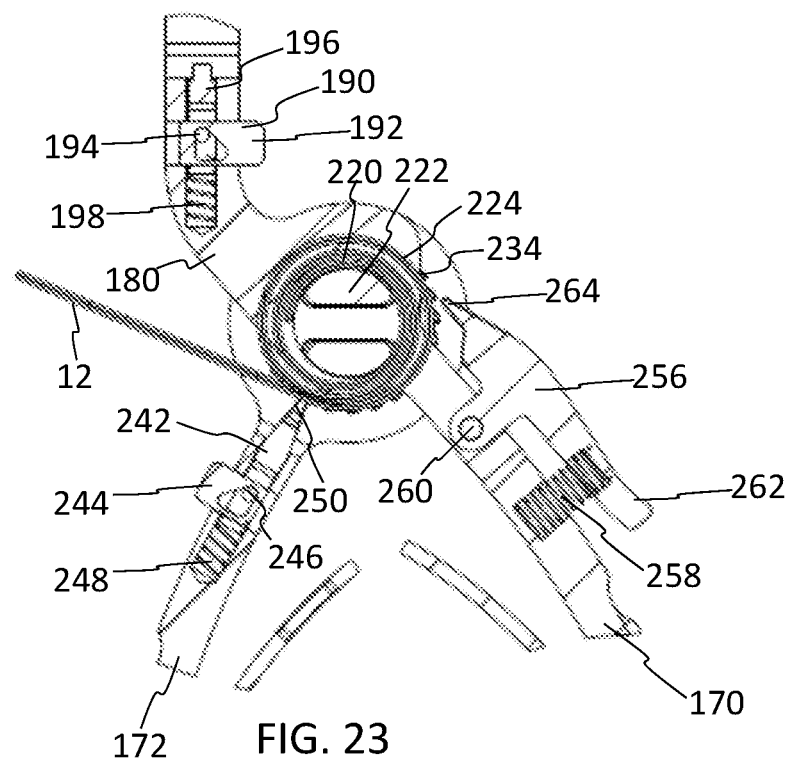
FIG. 23 is a partial cross-sectional view showing the flexible band wrapped around the spool of the ratcheting tensioner.

As shown in FIGS. 22-23, the ratcheting tensioner 104 is engaged with the clip inserter 102 with button assembly 190. The flexible band 12 is fed thru the band clamp implant 106 and the band clamp 106 is placed onto the rod 108 with the collar 122 of the clip inserter 102. The flexible band 12 is fed between the two halves 232 of the spool 222 of the ratcheting assembly 220. The handles 170, 172 of the ratcheting tensioner 104 are then actuated to wrap the flexible band 12 around the spool 222, thereby pulling the flexible band 12 thru the band clamp 106 and applying tension. Once a sufficient amount of tension is achieved, the driver shaft 138 may be passed though the clip inserter 102 into the set screw 114 on the band clamp 106 to lock the tension in the band 12. Tension may be removed from the flexible band 12 by unwinding the spool 222. In order to do this, the release arm 256 and actuator button 244 are depressed to disengage the ratchets 224 and the spool 222 is rotated manually to unwind the spool 222.

During the procedure, the band 12 may be threaded through the implant 106 and through the gap 230 in the spool 222 of the ratcheting tensioner 104. The band 12 may be looped around a portion of bone, such as the lamina or transverse process. Tension may be applied to the band 12 by squeezing the handles 170, 172 of the ratcheting tensioner 104. As the spool 222 rotates, the band 12 wraps around the spool 222 applying controlled, incremental tension to the band 12. Once the desired tension has been reached, the band 14 may be secured by the implant 106 (e.g., with a set screw 114 in the clamp 106), and the instrument 100 may be removed from the patient.

Figure 24:
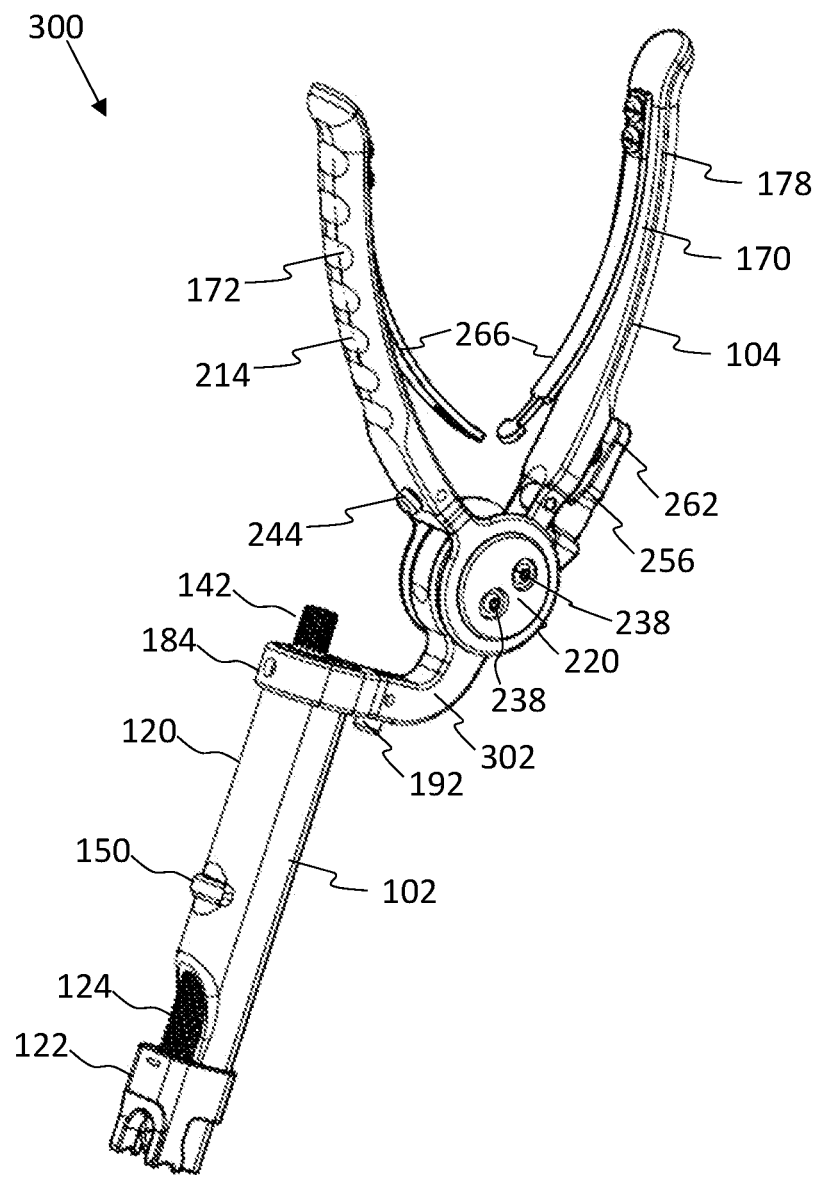
FIG. 24 shows a perspective view of an overhead ratcheting tensioner according to one embodiment.
Figure 25:
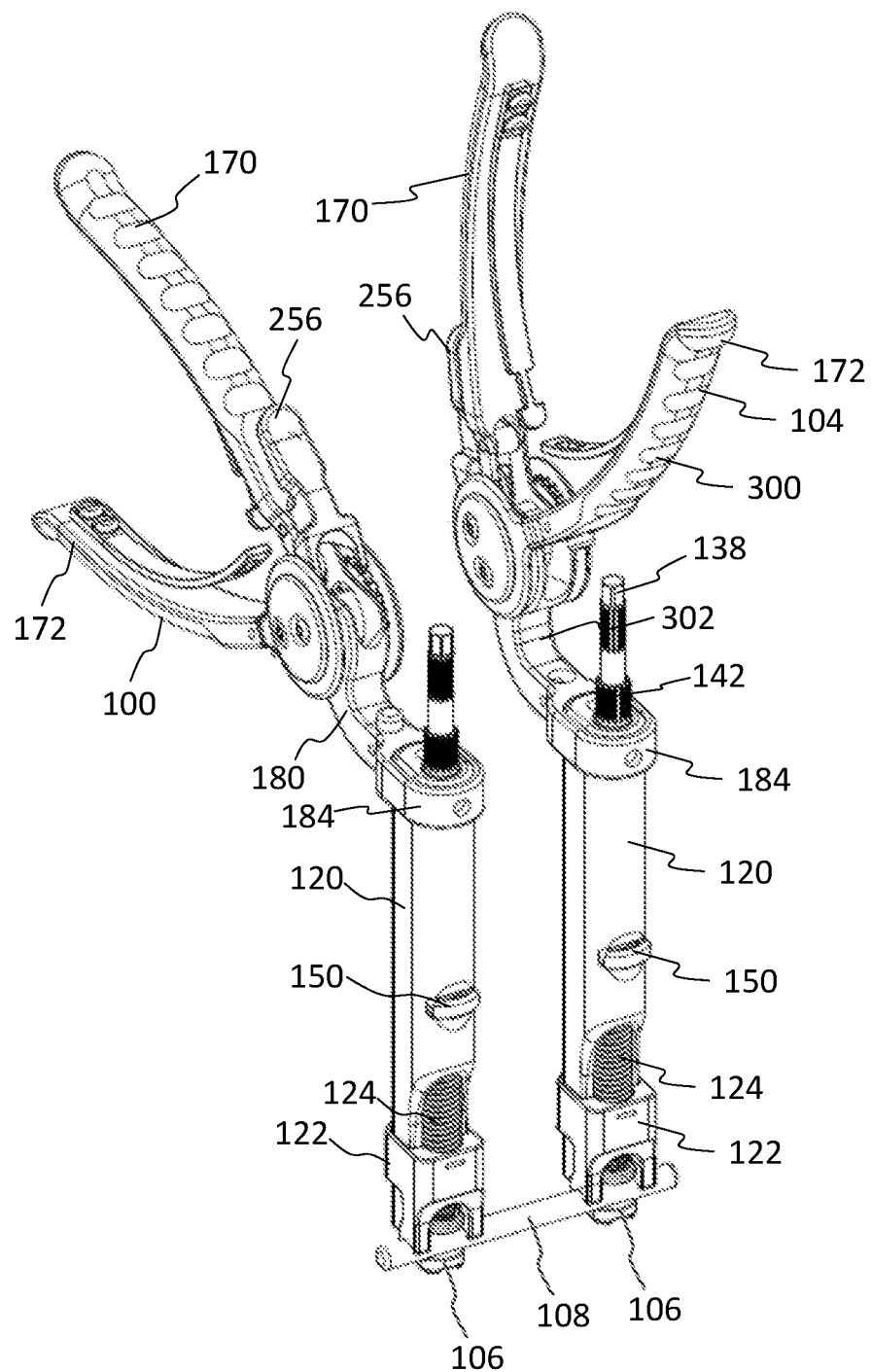
FIG. 25 shows a system of tensioning a spinal construct using the grip style ratcheting tensioner of FIG. 8 and the overhead style ratcheting tensioner of FIG. 24.

Turning now to FIGS. 24 and 25, an alternative version of a tensioner instrument system 300 is shown, which is the same as tensioner 100, except with a different overhead style grip configuration. Similar to the pistol grip style tensioner system 100, the overhead style tensioner system 300 includes the clip inserter 102 and ratcheting tensioner 104. In tensioner system 300, however, the ratcheting tensioner 104 is configured to be placed in an overhead orientation with respect to the clip inserter 102. For the overhead system 300, the ratcheting tensioner 104 is configured to be placed in the overhead orientation because the neck 302 of the fixed handle 170 is angled opposite of neck 180. For example, the neck 302 of tensioner system 300 is angled or curved back toward the pivoting handle 172.

As shown in FIG. 25, the overhead style tensioner system 300 offers the surgeon another option depending on their preference of hand position during tensioning of the flexible band 12. If desired, the overhead style tensioner system 300 may be used in conjunction with the pistol grip style tensioner 100. Band clamps 106 may be used at sequential spinal levels in order to reduce a deformity and anatomy may dictate that the band clamps 106 are positioned within close proximity to one another. Therefore, it may be advantageous to offer both styles of ratcheting tensioner 100, 300 in order to give space for the surgeon's hands.

The systems described herein allow surgeons to tension the flexible band in order to correct spinal deformities and achieve fixation. The instruments offer easy engagement with the band clamps and flexible bands, which may save time, for example, compared to instruments that use secondary locking steps for the band clamps or flexible bands. The tensioning instruments allow for essentially limitless tensioning capacity, which may be an improvement over instruments limited by the travel range of threaded mechanisms, for example. The tensioners may save the surgeon time during surgery as the tensioner does not need to be reset during correction. In addition, the handle mechanisms may allow for ease of use without the need for additional actuating instruments. The variety of configurations may also allow the surgeon to customize the implementation of instruments to the patient in order to optimize visualization of the surgical site.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. A tensioner instrument for tensioning a band, the instrument comprising:
    first and second pivoting arms extending from a proximal end to a distal end, the first and second pivoting arms having handles near the proximal ends, a base having a generally L-shaped body coupled to the first and second pivoting arms, and a ratchet positioned between the proximal ends of the first and second pivoting arms,
    wherein the base defines a slot to retain the band and guide the distal end of the first pivoting arm and the second pivoting arm defines an opening located beneath the slot and sized and dimensioned to receive the band, and the base includes a first elongate portion and a second elongate portion angled relative to the first elongate portion at a corner that couples with the first pivoting arm at a first hinge, and
    wherein when the handles are compressed together, the band is pinched in the slot between the distal end of the first pivoting arm and the base, and a distance between the distal ends of the arms is increased, thereby applying a tension to the band.

2. The tensioner instrument of claim 1, wherein the second elongate portion of the base terminates at a free end, which couples with the second pivoting arm at a second hinge.

3. The tensioner instrument of claim 1, wherein the first hinge moves the first pivoting arm towards the base and the second hinge moves the base away from the second pivoting arm.

4. The tensioner instrument of claim 3, wherein the ratchet is a linear ratchet.

5. The tensioner instrument of claim 4, wherein the ratchet includes a plurality of teeth along an interior of the ratchet.

6. The tensioner instrument of claim 5, wherein a pawl in the slot engages the teeth to thereby incrementally maintain the position of the first and second pivoting arms and the amount of tension applied to the band.

7. The tensioner instrument of claim 1, wherein a first end of the ratchet is coupled to one of the first and second pivoting arms via a pivot pin.

8. The tensioner instrument of claim 7, wherein the opposite end of the ratchet is positionable through a slot in the other of the first and second pivoting arms.

9. A tensioner instrument for tensioning a band, the instrument comprising:
    a first pivoting arm and a second pivoting arm, each extending from a proximal end to a distal end;
    a base coupled to the first and second pivoting arms; and
    a ratchet positioned between the proximal ends of the first and second pivoting arms,
    wherein the base defines a slot to retain the band and guide the distal end of the first pivoting arm and the second pivoting arm defines an opening located beneath the slot and sized and dimensioned to receive the band, and the base includes a first elongate portion and a second elongate portion angled relative to the first elongate portion at a corner that couples with the first pivoting arm at a first hinge.

10. The tensioner instrument of claim 9, wherein the second elongate portion of the base terminates at a free end, which couples with the second pivoting arm at a second hinge.

11. The tensioner instrument of claim 9, wherein the first hinge moves the first pivoting arm towards the base and the second hinge moves the base away from the second pivoting arm.

12. The tensioner instrument of claim 11, wherein the ratchet is a linear ratchet.

13. The tensioner instrument of claim 12, wherein the ratchet includes a plurality of teeth along an interior of the ratchet.

14. The tensioner instrument of claim 13, wherein a pawl in the slot engages the teeth to thereby incrementally maintain the position of the first and second pivoting arms and the amount of tension applied to the band.

15. The tensioner instrument of claim 9, wherein a first end of the ratchet is coupled to one of the first and second pivoting arms via a pivot pin.

16. The tensioner instrument of claim 15, wherein the opposite end of the ratchet is positionable through a slot in the other of the first and second pivoting arms.

\* \* \* \* \*